US008563259B2

(12) United States Patent
Lambris et al.

(10) Patent No.: US 8,563,259 B2
(45) Date of Patent: Oct. 22, 2013

(54) COMPLEMENT-MEDIATED THROMBOPHILIC ASSAY

(75) Inventors: John D. Lambris, Bryn Mawr, PA (US); Konstantinos Ritis, Alexndroupolis (GR)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 549 days.

(21) Appl. No.: 12/665,989

(22) PCT Filed: Jun. 25, 2008

(86) PCT No.: PCT/US2008/007877
§ 371 (c)(1),
(2), (4) Date: Aug. 24, 2010

(87) PCT Pub. No.: WO2009/005651
PCT Pub. Date: Jan. 8, 2009

(65) Prior Publication Data
US 2010/0311086 A1 Dec. 9, 2010

Related U.S. Application Data

(60) Provisional application No. 60/937,743, filed on Jun. 29, 2007.

(51) Int. Cl.
*G01N 33/00* (2006.01)
(52) U.S. Cl.
CPC ...................................... *G01N 33/00* (2013.01)
USPC ........... 435/7.25; 435/7.1; 435/7.92; 436/501
(58) Field of Classification Search
None
See application file for complete search history.

(56) References Cited

U.S. PATENT DOCUMENTS

| | | | |
|---|---|---|---|
| 4,444,879 A * | 4/1984 | Foster et al. | 435/7.95 |
| 5,420,016 A * | 5/1995 | Boguslaski et al. | 435/12 |
| 6,180,370 B1 | 1/2001 | Queen et al. | |
| 6,319,897 B1 | 11/2001 | Lambris et al. | |
| 7,491,530 B2 | 2/2009 | Dessain et al. | |
| 7,579,432 B2 | 8/2009 | Taylor et al. | |
| 2007/0026467 A1 | 2/2007 | Greenfield et al. | |
| 2012/0004393 A1* | 1/2012 | Lambris et al. | 530/324 |

FOREIGN PATENT DOCUMENTS

| | | |
|---|---|---|
| WO | WO 9913899 | 3/1999 |
| WO | WO 2004026328 | 4/2004 |
| WO | WO 2007062249 | 5/2007 |
| WO | WO 2009005651 | 1/2009 |

OTHER PUBLICATIONS

Allegretti, M., et al., "Targeting C5a: Recent Advances in Drug Discovery", Current Medicinal Chemistry, vol. 12, pp. 217-236 (2005).
Bird, R.E., et al., "Single-Chain Antigen-Binding Proteins", Science, vol. 242, pp. 423-426 (1988).
Burton, D.R., et al., "Human Antibodies From Combinatorial Libraries", Advances in Immunology, vol. 57, pp. 191-280 (1994).
Gu, et al., "Construction and Expression of Mouse-Human Chimeric Antibody SZ-51 Specific for Activated Platelet P-Selectin", Thrombosis and Hematocyst, vol. 77, pp. 755-759 (1997).
Hammel, M., et al., "Characterization of Ehp, a Secreted Complement Inhibitory Protein From *Staphylococcus aureus*", Journal Biological Chemistry, vol. 282, pp. 30051-30061 (2007).
Huston, E., et al., "Protein Engineering or Antibody Sites: Recovery of specific Activity in an Anti-Digoxin Single-Chain Fv Analogue Produced in *Escherichia coli*", Proc. Natl. Acad. Sci. USA, vol. 85, pp. 5879-5883 (1988).
Lee, L.Y., et al., "Identification and Characterization of the C3 Binding Domain of the *Staphylococcus aureus* Extracellular Fibrinogen-Binding Protein (Efb)", Journal of Biological Chemistry., vol. 279, pp. 50710-50716 (2004).
Morikis, D., et al., "Design, Structure, Function and Application of Compstatin", In Bioactive Peptides in Drug Discovery and Design: Medical Aspects, Matsoukas et al., Eds., IOS Press, pp. 235-246 (1999).
Morikis, D., et al., "Structural Aspects and Design of Low-Molecular-Mass Complement Inhibitors", Biochemical Society., vol. 30, pp. 1026-1036 (2002).
Proctor, L.M., et al., "Transdermal Pharmacology of Small Molecule Cyclic C5a Antagonists", Advances in Experimental Medicine and Biology, vol. 586, pp. 329-345 (2006).
Ritis, K., et al., "A Novel C5a Receptor—Tissue Factor Cross-Talk in Neutrophils Links Innate Immunity to Coagulation Pathways", The Journal of Immunology, vol. 177, pp. 4794-4802 (2006), Oct. 2006.
Tuszynski, G.P., et al., "Thrombospondin Promotes Platelet Aggregation", Blood, vol. 72, pp. 109-115 (1988).
Wright, A., et al., "Genetically Engineered Antibodies: Progress and Prospects", Critical Reviews in Immunology, vol. 12(3,4), pp. 125-168 (1992).
International Search Report and Written Opinion in PCT/US2008/007877, mailed Jul. 23, 2009.

* cited by examiner

*Primary Examiner* — Gary W Counts
(74) *Attorney, Agent, or Firm* — Potter Anderson and Corroon LLP

(57) ABSTRACT

A method for assessing the presence of an acquired thrombophilia disorder in a patient exhibiting hypercoagulation is disclosed.

11 Claims, 1 Drawing Sheet

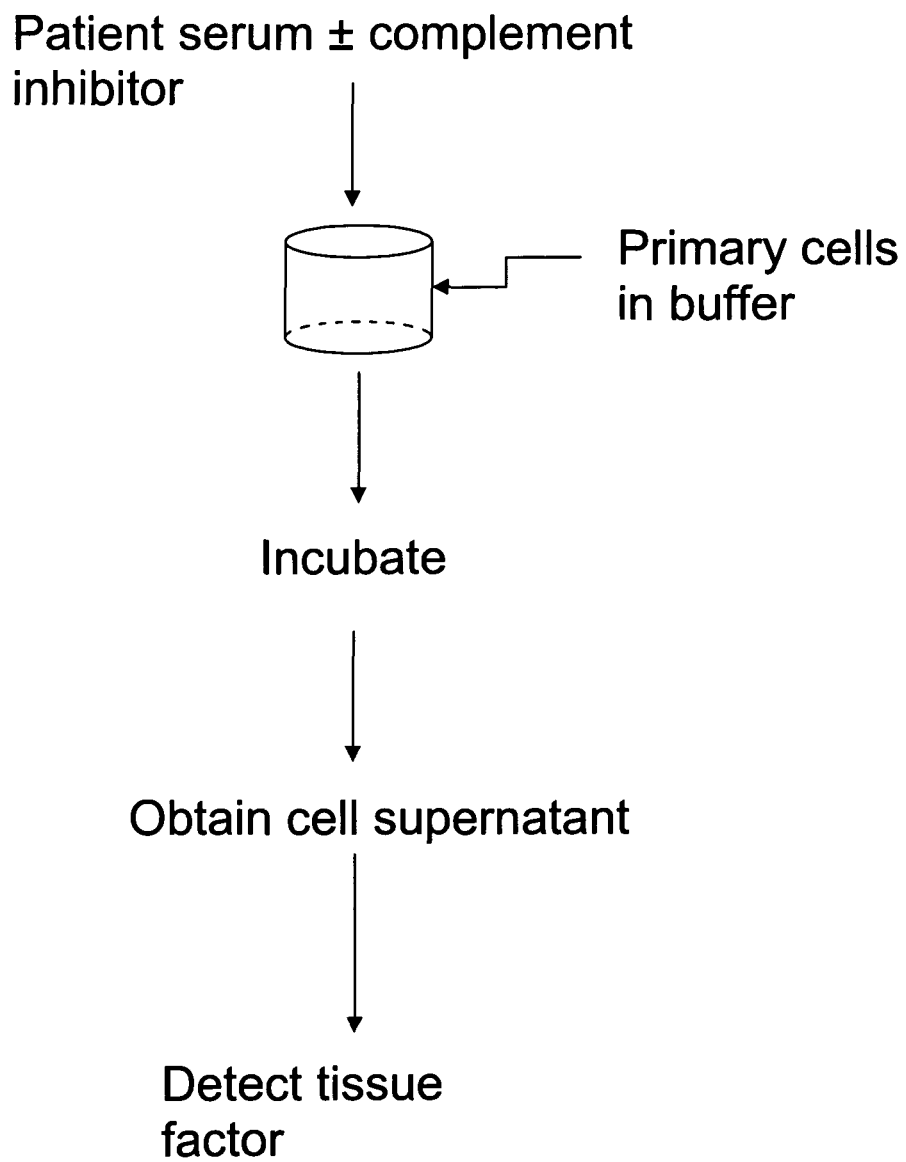

SEQUENCE LISTING

<160> NUMBER OF SEQ ID NOS: 3

<210> SEQ ID NO 1
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: DISULFID
<222> LOCATION: (2)..(12)

<400> SEQUENCE: 1

Ile Cys Val Val Gln Asp Trp Gly His His Arg Cys Thr
1               5                   10

```
<210> SEQ ID NO 2
<211> LENGTH: 16
<212> TYPE: PRT
<213> ORGANISM: Artificial Sequence
<220> FEATURE:
<223> OTHER INFORMATION: synthetic sequence
<220> FEATURE:
<221> NAME/KEY: VARIANT
<222> LOCATION: (1)..(1)
<223> OTHER INFORMATION: Xaa is Gly or is missing
<220> FEATURE:
<221> NAME/KEY: VARIANT
<222> LOCATION: (2)..(2)
<223> OTHER INFORMATION: Xaa is Ile, Val, Leu, Ac-Ile, Ac-Val or Ac-Leu
<220> FEATURE:
<221> NAME/KEY: DISULFID
<222> LOCATION: (3)..(13)
<220> FEATURE:
<221> NAME/KEY: VARIANT
<222> LOCATION: (5)..(5)
<223> OTHER INFORMATION: Xaa is Trp or an analog of Trp
<220> FEATURE:
<221> NAME/KEY: VARIANT
<222> LOCATION: (10)..(10)
<223> OTHER INFORMATION: Xaa is His, Ala, Phe or Trp
<220> FEATURE:
<221> NAME/KEY: VARIANT
<222> LOCATION: (14)..(14)
<223> OTHER INFORMATION: Xaa is L-Thr, D-Thr, Ile, Val or Gly
<220> FEATURE:
<221> NAME/KEY: VARIANT
<222> LOCATION: (15)..(15)
<223> OTHER INFORMATION: Xaa is Asn or Ala, or is missing
<220> FEATURE:
<221> NAME/KEY: VARIANT
<222> LOCATION: (16)..(16)
<223> OTHER INFORMATION: Xaa is Asn, or is missing

<400> SEQUENCE: 2

Xaa Xaa Cys Val Xaa Gln Asp Trp Gly Xaa His Arg Cys Xaa Xaa Xaa
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: synthetic sequence
<220> FEATURE:
<221> NAME/KEY: VARIANT
<222> LOCATION: (1)..(1)
<223> OTHER INFORMATION: Xaa is Gly or is missing
<220> FEATURE:
<221> NAME/KEY: VARIANT
<222> LOCATION: (2)..(2)
<223> OTHER INFORMATION: Xaa is Ile, Val, Leu, Ac-Ile, Ac-Val or Ac-Leu
<220> FEATURE:
<221> NAME/KEY: DISULFID
<222> LOCATION: (3)..(13)
<220> FEATURE:
<221> NAME/KEY: VARIANT
<222> LOCATION: (5)..(5)
<223> OTHER INFORMATION: Xaa is Trp or an analog of Trp
<220> FEATURE:
<221> NAME/KEY: VARIANT
<222> LOCATION: (8)..(8)
<223> OTHER INFORMATION: Xaa is Trp or an analog of Trp
<220> FEATURE:
<221> NAME/KEY: VARIANT
<222> LOCATION: (10)..(10)
<223> OTHER INFORMATION: Xaa is His, Ala, Phe or Trp
<220> FEATURE:
<221> NAME/KEY: VARIANT
<222> LOCATION: (14)..(14)
<223> OTHER INFORMATION: Xaa is L-Thr, D-Thr, Ile, Val or Gly
<220> FEATURE:
<221> NAME/KEY: VARIANT
<222> LOCATION: (15)..(15)
```

```
<223> OTHER INFORMATION: Xaa is Asn or Ala, or is missing
<220> FEATURE:
<221> NAME/KEY: VARIANT
<222> LOCATION: (16)..(16)
<223> OTHER INFORMATION: Xaa is Asn, or is missing

<400> SEQUENCE: 3

Xaa Xaa Cys Val Xaa Gln Asp Xaa Gly Xaa His Arg Cys Xaa Xaa Xaa
1               5                   10                  15
```

COMPLEMENT-MEDIATED THROMBOPHILIC ASSAY

Pursuant to 35 U.S.C. §202(c), it is acknowledged that the United States government may have certain rights in the invention described herein, which was made in part with funds from the National Institutes of Health under Grant Number GM62134.

FIELD OF THE INVENTION

This invention relates to the field of thrombotic disorders. In particular, a diagnostic method is provided for the differential diagnosis of acquired thrombotic disorders.

BACKGROUND OF THE INVENTION

Various publications, including patents, published applications, technical articles and scholarly articles are cited throughout the specification. Each of these cited publications is incorporated by reference herein, in its entirety. Full citations for publications not cited fully within the specification are set forth at the end of the specification.

A hypercoagulable disorder is a condition that increases the risk of inappropriate or excessive thrombos (blood clot) formation in a patient. Hypercoagulation-related disorders are divided in two major categories. The first includes the inherited hypercoagulable states, such as Factor V Leiden; prothrombin gene mutation; elevated levels of fibrinogen; deficiencies of anticoagulant proteins, such as antithrombin, protein C and protein S; sticky platelets and abnormal fibrinolytic system, including hypoplasminogenia, dyspasminogenia, and elevation in levels of PAI-1. The second category of hypercoagulation-related disorders includes the acquired hypercoagulable diseases. These diseases result from reversible or irreversible causes, including: cancer and cancer related disorders, such as adenocarcinomas, metastatic cancer, cancer treatment, hematological malignancies (i.e., myeloproliferative disorders, paroxysmal nocturnal hemoglobinuria and hyperviscosity syndromes); autoimmune disorders, such as antiphospholipid antibody syndrome (APS), systemic lupus erythematosus (SLE), inflammatory bowel diseases, heparin-induced thrombocytopenia and vasculitis; acute infection and sepsis; recent trauma or surgery; prolonged bedrest or inactivity; long air travel; atherosclerosis; hypertension; nephrotic syndrome; pregnancy; extracorporeal circulation; artificial vascular devices; obesity; and previous deep vein thrombosis or pulmonary embolism.

Hypercoagulable states (also called thrombophilias, thrombotic disorders and prothrombotic disorders) with consequent thrombotic manifestations, constitute a major life threatening clinical problem. Although there are functional tests to support the differential diagnosis of some inherited hypercoagulable states, currently no specific functional test exists to support the diagnosis of acquired thrombotic disorder. In recent years, advances in understanding of the natural anticoagulant and fibrinolytic system have been translated into preliminary diagnostic tools known as "thrombotic" or "thrombophilic" tests. However, the algorithmic diagnostic procedure generally used today in efforts to solve clinical problems related to hypercoagulation does not include "thrombotic" tests, because there is no specific thrombophilic laboratory profile of hypercoagulable and thrombotic disorders. Furthermore, the high cost and laborious technology involved have further hindered the practical clinical application of such assays.

Thus, there is a need in the art for an assay that is useful in the differential diagnosis of acquired thrombophilia disorder.

SUMMARY OF THE INVENTION

One aspect of the invention features a method for assessing the presence of an acquired thrombophilia disorder in a patient exhibiting hypercoagulation. The method comprises the steps of: (a) incubating primary healthy blood cells in a first incubation condition, the first incubation condition comprising the presence of serum obtained from the patient; (b) incubating primary healthy blood cells in a second incubation condition, the second incubation condition comprising the presence of serum obtained from the patient, wherein the serum further comprises a complement inhibitor; and (c) detecting the presence of tissue factor in the first incubation condition and in the second incubation condition, wherein the presence of tissue factor in the first incubation condition and not in the second incubation condition is indicative of an acquired thrombophilia disorder in the patient.

In one embodiment, tissue factor may be detected directly in the incubation reactions, such as by exposing the reaction mixtures to an agent capable of distinguishing tissue factor-containing cells from other cells, e.g., via fluorescence-activated cell sorting, or by exposing the reaction mixtures to an agent capable of binding tissue factor, e.g., anti-tissue factor antibodies or functional fragments thereof.

In one embodiment, the detecting step comprises detecting the presence of tissue factor in a first cell supernatant and in a second cell supernatant, wherein the first cell supernatant is obtained from the first incubation condition and the second cell supernatant is obtained from the second incubation. In one embodiment, detecting the presence of tissue factor in a first cell supernatant and in a second cell supernatant comprises measuring a first rate of coagulation using the first cell supernatant and a second rate of coagulation using the second cell supernatant, wherein an acquired thrombophilia disorder is indicated in the patient if the first rate of coagulation is accelerated compared to the second rate of coagulation.

In preferred embodiments, the complement inhibitor is a C3 inhibitor. Examples of C3 inhibitors include compstatin, a compstatin analog, a compstatin peptidomimetic, a compstatin derivative, and combinations thereof.

In other preferred embodiments, the complement inhibitor is a C5aR inhibitor. Examples of C5aR inhibitors include an anti-C5 antibody, an anti-C5 aptamer, an anti-C5aR antibody and a C5aR antagonist. Examples of a C5aR antagonist include PMX-53 and analogs thereof.

Acquired thrombophilia disorders that may be assessed in the method of the invention include antiphospholipid syndrome and systemic lupus erythymatosus, among others.

Another aspect of the invention features a kit comprising a complement inhibitor and at least one agent for detecting the presence of tissue factor. In one embodiment, the complement inhibitor is a C3 inhibitor. In certain embodiments, the agent for detecting the presence of tissue factor is a reagent for labeling tissue factor-containing cells for fluorescence-activated cell sorting. In other embodiments, the agent for detecting the presence of tissue factor is an anti-tissue factor antibody or functional fragment thereof. In still other embodiments, agents for detecting the presence of tissue factor comprise reagents for performing a functional assay, such as a tissue factor-dependent coagulation assay. The kit may further comprise instructions for use of the complement inhibitor and at least one agent for detecting the presence of tissue factor in a method for assessing the presence of an acquired thrombophilia disorder in a patient exhibiting hypercoagulation, such as the method described above.

Other features and advantages of the invention will be understood by reference to the drawings, detailed description and examples that follow.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1 depicts schematically the steps of the method of the invention.

DETAILED DESCRIPTION OF ILLUSTRATIVE EMBODIMENTS

The invention provides a method that is useful in the differential diagnosis of the basis for hypercoagulation in a patient exhibiting hypercoagulation. Specifically, the method provides an assessment of whether hypercoagulation is likely to be due to an acquired thrombophilia disorder, rather than an inherited hypercoagulable disease or disorder.

Various terms relating to the methods and other aspects of the present invention are used throughout the specification and claims. Such terms are to be given their ordinary meaning in the art unless otherwise indicated. Other specifically defined terms are to be construed in a manner consistent with the definition provided herein.

Definitions:

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well known and commonly employed in the art.

Standard techniques are used for nucleic acid and peptide synthesis. The techniques and procedures are generally performed according to conventional methods in the art and various general references (e.g., Sambrook and Russell, 2001, Molecular Cloning, A Laboratory Approach, Cold Spring Harbor Press, Cold Spring Harbor, N.Y., and Ausubel et al., 2007, Current Protocols in Molecular Biology, John Wiley & Sons, NY), which are provided throughout this document.

The nomenclature used herein and the laboratory procedures used in analytical chemistry and organic syntheses described below are those well known and commonly employed in the art. Standard techniques or modifications thereof, are used for chemical syntheses and chemical analyses.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations would be understood by the skilled artisan as appropriate to practice the present invention.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. The antibodies useful in the present invention may exist in a variety of forms including, for example, polyclonal antibodies, monoclonal antibodies, intracellular antibodies ("intrabodies"), Fv, Fab and F(ab)$_2$, as well as single chain antibodies (scFv), camelid antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

As used herein, a "complement inhibitor" is a molecule that prevents or significantly reduces the induction of tissue factor expression by activated complement.

As used herein, a "C3 inhibitor" is a molecule that prevents or reduces the cleavage of C3 into C3a and C3b.

As used herein, a "C5aR inhibitor" is a molecule that prevents or reduces the binding of C5a to the C5a receptor.

As used herein, a "Factor D inhibitor" is a molecule that prevents or reduces the activity of Factor D.

A "primary cell" refers to a cell taken directly from an organism and before the first subculture step.

As used herein, "subculture" refers to the transfer of cells from one growth container to another growth container.

As used herein, a "passage" refers to a round of subculturing. Thus, when cells are subcultured, they are referred to as having been passaged.

It is understood that any and all whole or partial integers between any ranges set forth herein are included herein.

Description:

Diagnosis is the process of identifying a disease by its signs, symptoms and results of various diagnostic procedures. Differential diagnosis is the process of distinguishing between two or more diseases and conditions with similar symptoms. As the skilled artisan is aware, differential diagnosis seldom relies on a single test or assay, but rather, results from an accumulation of indicators consistent with a particular diagnosis. The invention provides a method useful as an indicator for diagnosing the cause of hypercoagulation in a patient.

The invention springs in part from the discovery of the pathophysiological mechanisms that trigger and regulate the extrinsic coagulation system. Extrinsic coagulation is an inducible signaling cascade that is activated by tissue factor (TF) upregulation occurring as a result of exposure to clotting zymogen FVII, subsequent to inflammation or tissue damage. TF (also called thromboplastin) is induced by inflammatory mediators in monocytes, neutrophils, and endothelial cells. Complement is one of the inflammatory mediators that induces TF expression. The invention provides a method for assessing the origin and regulation of TF in a patient exhibiting hypercoagulation based on the effect of serum from the patient on expression of tissue factor in primary blood cells obtained from a healthy subject. In addition to providing an indication of the presence of an acquired thrombophilia disorder, thereby addressing a need in the art, the method advantageously is relatively inexpensive and is not labor or time intensive.

The method of the invention typically comprises the following steps (FIG. 1). First, serum is obtained from the blood of a patient exhibiting hypercoagulation. Healthy primary blood cells are incubated with the patient serum and, in parallel, with patient serum which has been pre-treated with a complement inhibitor. After a period of incubation, the expression of tissue factor by the primary blood cells is assessed. If the patient has an acquired thrombophilia disorder manifested by activated complement in the bloodstream, the patient's serum comprises activated complement, which will induce tissue factor expression in the primary blood cells. Inhibition of the activated complement precludes the induction of tissue factor expression. Therefore, the induction by patient serum of tissue factor in the healthy primary blood cells is indicative that the patient has an acquired thrombophilia disorder characterized by activated complement.

Tissue factor induction can be measured in a wide variety of ways known to the skilled artisan. Tissue factor has two known isoforms: a 47-kD cell surface protein and an alternatively-spliced variant (206 aa) which is soluble and biologically active. For instance, any method known in the art for detecting a protein may be used for assessing the presence of tissue factor. Fluorescence activated cell sorting (FACS) is useful for detecting tissue factor induction by detecting cells having cell-surface tissue factor. Immunoassays are also useful for detecting tissue factor. Immunoassays include, for example, immunohistochemistry assays, immunocytochemistry assays, ELISA, capture ELISA, sandwich assays, enzyme immunoassay, radioimmunoassay, fluorescent immunoassay, and the like, all of which are known to those of skill in the art. See e.g. Harlow et al., 1988, Antibodies: A Laboratory Manual, Cold Spring Harbor Laboratory Press, Cold Spring Harbor, N.Y.; Harlow et al., 1999, Using Antibodies: A Laboratory Manual, Cold Spring Harbor Laboratory Press, Cold Spring Harbor, N.Y. The presence of tissue factor transcripts may also be detected by methods well known in the art, including hybridization methods and RT-PCR methods.

Functional assays may be used to test for the presence of tissue factor. In a particular embodiment of the method, tissue factor is detected by a functional assay, such as a tissue factor-responsive coagulation assay. In a certain embodiment of the functional assay, the rate of coagulation is measured in a modified prothrombin test that includes the use of an aliquot of supernatant obtained from the healthy primary cells incubated with patient serum. In the classic PT assay, prothrombin time reagent containing thromboplastin (another name for tissue factor) and calcium chloride is mixed with patient plasma, and the time to clot formation of the resulting mixture is measured photo-optically.

The modified prothrombin time (mPT) assay useful in the present invention differs in several aspects. First, platelet-poor plasma is obtained from a healthy patient (e.g., patient having normal clotting) using conventional methods known in the art. For instance, whole blood is collected in tubes treated with citrate anti-coagulant and is centrifuged for 10 minutes at 2000 g. The resulting supernatant comprises platelet-poor plasma. Second, the amount of thromboplastin solution is reduced. Reducing the amount of thromboplastin slows down the rate of clotting, therefore the time to clot is longer. This modification enables accurate and reproducible coagulation measurements. A cell supernatant is obtained from the incubated healthy primary blood cells by any method known in the art. Nonlimiting examples of such methods include centrifugation (e.g., 1000×g for 10 minutes) and magnetic bead separation. The mPT assay is carried out by combining plasma, the reduced amount of thromboplastin solution and an aliquot of cell supernatant from one of the two incubation conditions, and measuring the clotting time. If the rate of coagulation ($A_y$) for cell supernatant from the cells incubated with patient serum with a complement inhibitor is approximately the same as the rate ($A_n$) for cell supernatant from the cells incubated with patient serum without a complement inhibitor, the hypercoagulation present in the patient does not result from an acquired thrombophilic disorder characterized by activated complement in the bloodstream. If, however, the cell supernatant from the cells incubated with patient serum without a complement inhibitor is accelerated compared to the rate for cell supernatant from the cells incubated with patient serum with a complement inhibitor, the hypercoagulation present in the patient does result from an acquired thrombophilic disorder characterized by activated complement in the bloodstream. Table 1 summarizes this analysis.

TABLE 1

|  | Complement inhibitor added to serum? | Rate of coagulation | Time to clot |
|---|---|---|---|
| Patient | No | $A_n$ | $a_n$ |
|  | Yes | $A_y$ | $a_y$ |
| Healthy or without an acquired thrombophilia disorder |  | $A_n \approx A_y$ | $a_n \approx a_y$ |
| Acquired thrombophilic disorder |  | $A_n > A_y$ | $a_n < a_y$ |

The method of the invention may be practiced with any vertebrate having a complement system, including but not limited to, non-mammals and mammals. Mammals include humans, non-human primates, goats, sheep, horses, mice, rats and the like. Preferably, the method is practiced with serum from a human patient.

Primary blood cells useful in the practice of the invention include neutrophils and monocytes. Peripheral blood mononuclear cells (PMBCs) comprise monocytes and may also be used in the practice of the invention. Primary blood cells are obtained by methods known in the art. Such methods typically include obtaining a sample of blood, for instance, by venous puncture, treating the sample with an-anti-clotting agent, such as EDTA, and then density-gradient centrifugation. See, for instance, Ritis et al., 2006, J. Immunol. 177: 4794-4802. Other methods of isolating cells include cell sorting techniques, such as fluorescence activated cell sorting (FACS), and bulk separation methods, such as panning and magnetic bead separations. However, the method of the invention should not be construed as limited by the method of obtaining primary blood cells. Preferably, the primary blood cells are of the same species as the patient whose serum is tested. Other cells that produce tissue factor in response to activated complement may be used instead of, or in addition to, primary blood cells in the assay of the invention. Nonlimiting examples of such cells human umbilical vein endothelial cells (HUVEC) and the MEG-01 cell line.

Any complement inhibitor, as defined herein, may be used in the method of the invention. Complement inhibitors include, but are not limited to, C3 inhibitors, C5aR inhibitors and Factor D inhibitors. Inhibitors may act directly or indirectly. For instance, inhibition of the Eculizumab (Alexion Pharmaceuticals, Cheshire, Conn.), an anti-C5 antibody, inhibits the generation of C5a, the ligand for C5aR. Thus, Eculizumab indirectly inhibits C5aR. Pexelizumab, an scFv fragemnt of Eculizumab, has the same activity. Similarly, ARC1905 (Archemix), an anti-C5 aptamer, binds to and inhibits cleavage of C5, inhibiting the generation of C5a. Other examples of complement inhibitors are known in the art. Acetyl-Phe-[Orn-Pro-D-cyclohexylalanine-Trp-Arg] (AcF[OPdChaWR]; PMX-53; Peptech) is a small cyclic hexapeptide that is a C5aR antagonist. Analogs of PMX-53 (e.g., PMX-201 and PMX-205) that also function as C5aR antagonists are also available (see for instance Proctor et al., 2006, Adv. Exp. Med. Biol. 586:329-45 and U.S. Pat. Pub. No. 20060217530). Neutrazumab (G2 Therapies) binds to C5aR, thereby inhibiting binding of C5a to C5aR. TNX-558 (Tanox) binds to and neutralizes C5a. Factor D is inhibited by diisopropyl fluorophosphate. TNX-234 (Tanox) binds to and inhibits Factor D. See also Morikis et al. 2002, Biochem Soc. 30:1026-1036 and Wetsel et al. in: Therapeutic Interventions in the Complement System, Vol. 9 (Lambris et al., eds) Humana Press, Totowa, N.J., 2000. Preferably, the complement inhibitor is a C3 inhibitor. Preferably, the C3 inhibitor is compstatin or a compstatin analog, derivative or peptidomimetic. Compstatin is a small molecular weight disulfide bonded cyclic peptide having the sequence Ile-Cys-Val-Val-Gln-Asp-Trp-Gly-His-His-Arg-Cys-Thr (SEQ ID NO. 1). Examples of compstatin analogs, derivates and peptidomimetics are described in the art. See, for instance, U.S. Pat. No. 6,319,897, WO/1999/013899, WO/2004/026328, WO/2007/062249 and Morikis et al., 1999, "Design, Structure, Function and Application of Compstatin" in Bioactive Peptides in Drug Discovery and Design: Medical Aspects, Matsoukas et al., eds., IOS Press, Amsterdam NL.

An exemplary compstatin analog comprises a peptide having a sequence: Xaa1-Cys-Val-Xaa2-Gln-Asp-Trp-Gly-Xaa3-His-Arg-Cys-Xaa4 (SEQ ID NO. 2); wherein:

Xaa1 is Ile, Val, Leu, Ac-Ile, Ac-Val, Ac-Leu or a dipeptide comprising Gly-Ile;

Xaa2 is Trp or a peptidic or non-peptidic analog of Trp;

Xaa3 is His, Ala, Phe or Trp; and

Xaa4 is L-Thr, D-Thr, Ile, Val, Gly, or a tripeptide comprising Thr-Ala-Asn, wherein a carboxy terminal —OH of any of the L-Thr, D-Thr, Ile, Val, Gly or Asn optionally is replaced by —NH$_2$; and the two Cys residues are joined by a disulfide bond. Xaa1 may be acetylated, for instance, Ac-Ile. Xaa2 may be a Trp analog comprising a substituted or unsubstituted aromatic ring component. Non-limiting examples include 2-napthylalanine, 1-naphthylalanine, 2-indanylglycine carboxylic acid, dihydrotryptophan or benzoylphenylalanine.

Another exemplary compstatin analog comprises a peptide having a sequence: Xaa1-Cys-Val-Xaa2-Gln-Asp-Xaa3-Gly-Xaa4-His-Arg-Cys-Xaa5 (SEQ ID NO. 3); wherein:

Xaa1 is Ile, Val, Leu, Ac-Ile, Ac-Val, Ac-Leu or a dipeptide comprising Gly-Ile; Xaa2 is Trp or an analog of Trp, wherein the analog of Trp has increased hydrophobic character as compared with Trp, with the proviso that, if Xaa3 is Trp, Xaa2 is the analog of Trp;

Xaa3 is Trp or an analog of Trp comprising a chemical modification to its indole ring wherein the chemical modification increases the hydrogen bond potential of the indole ring;

Xaa4 is His, Ala, Phe or Trp; and Xaa5 is L-Thr, D-Thr, Ile, Val, Gly, a dipeptide comprising Thr-Asn or Thr-Ala, or a tripeptide comprising Thr-Ala-Asn, wherein a carboxy terminal —OH of any of the L-Thr, D-Thr, Ile, Val, Gly or Asn optionally is replaced by —NH$_2$; and the two Cys residues are joined by a disulfide bond. The analog of Trp of Xaa2 may be a halogenated tryptophan, such as 5-fluoro-1-tryptophan or 6-fluoro-1-tryptophan. The Trp analog at Xaa2 may comprise a lower alkoxy or lower alkyl substituent at the 5 position, e.g., 5-methoxytryptophan or 5-methyltryptophan. In other embodiments, the Trp analog at Xaa 2 comprises a lower alkyl or a lower alkenoyl substituent at the 1 position, with exemplary embodiments comprising 1-methyltryptophan or 1-formyltryptophan. In other embodiments, the analog of Trp of Xaa3 is a halogenated tryptophan such as 5-fluoro-1-tryptophan or 6-fluoro-1-tryptophan.

Other C3 inhibitors include vaccinia virus complement control protein (VCP) and antibodies that specifically bind C3 and prevent its cleavage. Anti-C3 antibodies useful in the present invention can be made by the skilled artisan using methods known in the art. See, for instance, Harlow, et al. (1988, In: Antibodies, A Laboratory Manual, Cold Spring Harbor, N.Y.), Tuszynski et al. (1988, Blood, 72:109-115), U.S. patent publication 2003/0224490, Queen et al. (U.S. Pat. No. 6,180,370), Wright et al., (1992, Critical Rev. in Immunol. 12(3,4):125-168), Gu et al. (1997, Thrombosis and Hematocyst 77(4):755-759) and Burton et al., (1994, Adv. Immunol. 57:191-280). Anti-C3 antibodies are also commercially available. Other C3 inhibitors include C3-binding and complement inhibitory secreted S. aureus extracellular fibrinogen-binding protein Efb (Lee et al., 2004, J. Biol. Chem. 279: 50710-50716) and the Efb homologous protein, Ehp (Hammel et al., 2007, J. Biol. Chem. 282: 30051-30061.

The invention also includes a kit comprising a complement inhibitor and one or more compositions for measuring TF (thromboplastin) formation directly or indirectly, e.g., via rate of coagulation. Compositions for measuring the TF include, but are not limited to, anti-TF antibodies or functional fragments thereof, and components of prothrombin or modified prothrombin tests. The kit may further comprise an instructional material which describes the use of the complement inhibitor in an method assessing the presence of an acquired thrombophilia disorder in a patient exhibiting hypercoagulation. In one embodiment, the complement inhibitor is a C3 inhibitor. Optionally, the kit may further comprise at least one of a vessel for collecting a sample of blood, a container comprising plasma, a container suitable for incubating primary blood cells with patient serum, a composition comprising thromboplastin, and an excipient suitable for suspending or dissolving the composition comprising thromboplastin or the complement inhibitor, or any of the reagents of the kit. As used herein, an "instructional material" includes a publication, a recording, a diagram, or any other medium of expression which can be used to communicate the usefulness of the complement inhibitor in the kit assessing the presence of an acquired thrombophilia disorder in a patient exhibiting hypercoagulation.

The following example is provided to describe the invention in greater detail. It is intended to illustrate, not to limit, the invention.

EXAMPLE

To test serum for complement activating activity, serum was obtained from patients diagnosed with various disorders. Serum was obtained from patients diagnosed with: antiphospholipid syndrome (APS; n=26), systemic lupus erythymatosus (SLE; n=9), rheumatoid arthritis (n=12), sepsis (n=6), metastatic cancer (n=8) and inherited hypercoagulation (n=9). Serum was also obtained from healthy individuals (n=22).

Freshly obtained primary cells (monocytes or neutrophils) obtained from healthy donors were suspended in phosphate buffered saline (PBS). In parallel, the cells were stimulated with patient serum and with patient serum that was pre-incubated for 30 minutes with either 15 µM Compstatin or 10 µM C5aR antagonist to inhibit complement. The cells were incubated with serum for approximately 2 to 2.5 hours at 37° C. Subsequently, supernatant from the serum-incubated cells was obtained by centrifugation at 1000×g for 10 minutes. The supernatant was then assessed in a modified PT assay.

In a standard PT assay, 100 µl patient plasma is mixed with 200 µl commercial thromboplastin (International Sensitivity Index (ISI) 1.0 or ISI 1.9), and time of clotting is assessed by measuring in seconds the time required for clot formation after thromboplastin is added. In the modified PT (mPT) assay, 100 µl platelet-poor plasma (PPP) from a healthy subject was used and about 120-130 µl of the commercial thromboplastin (also called tissue factor) was replaced with PBS (the total volume of clotting reaction remains stable, at 300 µl) in order to obtain a technical prolongation of the clotting time from about 12-13 seconds to about 32-37 seconds. To test the effect of the test serum on TF expression of healthy primary blood cells, the about 120-130 µl PBS was replaced with about 120-130 µl of supernatant from the primary cells stimulated with test serum. All mPT assays were performed independently by two experienced physicians.

When complement is activated in the test serum, the use of 120-130 µl supernatant in the mPT test reduces the clotting time from about 32-37 sec to about 18-20 seconds. This reduction in clotting time occurs because TF expression is induced in the normal primary cells by the activated complement. When the activated complement in the test serum has been inhibited (e.g., with Compstatin or C5aR antagonist), TF expression is not induced by activated complement in normal primary cells and the mPT remains unchanged (about 32 to about 37 seconds). Results are summarized in Table 2.

TABLE 2

| Sera | Clotting time (in seconds) | | |
| --- | --- | --- | --- |
|  | No complement inhibitor | Compstatin | C5aR antagonist |
| Healthy donor serum (n = 22) | 32.03 ± 0.71 | 31.19 ± 0.16 (p = ns) | Not performed* |
| APS serum (n = 26) | 21.14 ± 1.91 | 31.11 ± 0.26 (p < 0.0001) | 31.67 ± 0.62 (p < 0.0001) |
| SLE serum (n = 9) | 22.07 ± 2.01 | 31.26 ± 0.17 (p < 0.0001) | 30.58 ± 0.47 (p < 0.0001) |
| Rheumatoid arthritis serum (n = 12) | 29.14 ± 1.85 | 30.26 ± 0.81 (p = ns) | Not performed* |
| Acute sepsis serum (n = 6) | 26.17 ± 1.08 | 28.97 ± 0.80 (p < 0.05) | 28.16 ± 0.44 (p < 0.0001) |

TABLE 2-continued

| Sera | Clotting time (in seconds) | | |
| --- | --- | --- | --- |
|  | No complement inhibitor | Compstatin | C5aR antagonist |
| Metastatic cancer serum (n = 8) | 25.74 ± 1.71 | 26.07 ± 1.21 (p = ns) | Not performed* |
| Inherited hypercoagulation serum (n = 9) | 28.91 ± 0.92 | 29.01 ± 1.08 (p < ns) | Not performed* |

*These disorders were not tested using antagonism of C5a receptor since no effect with compstatin was observed.

To verify that the thromboplastic activity in supernatant from the sera-treated cells is due to TF, the supernatants from the cells previously incubated separately with serum from 26 APS patients were incubated for 30 minutes with 1.100 of a specific anti-TF monoclonal antibody (#4509; American Diagnostics). Clotting was then assessed using the mPT assay as described. The anti-TF monoclonal antibody caused the clotting time to return to the baseline value (32-37 sec), indicating the thromboplastic activity in supernatant from the APS sera-treated cells is due to TF. Similar results were also observed for supernatant from SLE sera-treated cells.

Of the seven different sera, only sera from APS and SLE patients showed a complete loss of induction of TF expression in normal primary cells after complement inhibition. Sera from septic patients showed a partial inhibition of clotting time about treatment with Compstatin; the difference in clotting time before and after inhibition with compstatin in acute sepsis is about 30% of the time difference observed before and after inhibition with Compstatin for either APS or SLE serum. The sensitivity of the mPT test after Compstatin-mediated inhibition of complement was 100% in APS and SLE patients; that is, the pro-coagulant activity was completely abolished after inhibition with compstatin. In addition to demonstrating that activated complement in the serum of APS and SLE patients induces expression of TF in normal primary cells, the data also suggest that cytokines other than complement are responsible for TF induction in cancer patients. In addition, the data indicate that complement partially contributes to the hypercoagulability in septic patients. No changes in clotting time were observed in samples from patients with other diseases or from healthy donors, indicating that these sera do not contain activated complement.

The present invention is not limited to the embodiments described and exemplified above, but is capable of variation and modification within the scope of the appended claims.

What is claimed:

1. A method for assessing the presence of an acquired thrombophilia disorder in a patient exhibiting hypercoagulation, the method comprising:
   a) incubating primary healthy blood cells in a first incubation condition, the first incubation condition comprising the presence of serum obtained from the patient;
   b) incubating primary healthy blood cells in a second incubation condition, the second incubation condition comprising the presence of serum obtained from the patient, wherein the serum further comprises a complement inhibitor; and
   c) detecting the presence of tissue factor in the first incubation condition and in the second incubation condition, wherein the presence of tissue factor in the first incubation condition and not in the second incubation condition is indicative of an acquired thrombophilia disorder in the patient.

2. The method of claim 1, wherein the detecting step comprises contacting the incubation conditions with an agent capable of binding tissue factor.

3. The method of claim 2, wherein the agent is an anti-tissue factor antibody or functional fragment thereof.

4. The method of claim 1, wherein the detecting step comprises detecting the presence of tissue factor in a first cell supernatant and in a second cell supernatant, wherein the first cell supernatant is obtained from the first incubation condition and the second cell supernatant is obtained from the second incubation.

5. The method of claim 4, wherein detecting the presence of tissue factor in a first cell supernatant and in a second cell supernatant comprises measuring a first rate of coagulation using the first cell supernatant and a second rate of coagulation using the second cell supernatant, wherein an acquired thrombophilia disorder is indicated in the patient if the first rate of coagulation is accelerated compared to the second rate of coagulation.

6. The method of claim 1, wherein the complement inhibitor is a C3 inhibitor.

7. The method of claim 6, wherein the C3 inhibitor is selected from the group consisting of: compstatin, a compstatin analog, a compstatin peptidomimetic, a compstatin derivative, and combinations thereof.

8. The method of claim 1, wherein the complement inhibitor is a C5aR inhibitor.

9. The method of claim 8, wherein the C5aR inhibitor is selected from the group consisting of: an anti-C5 antibody, an anti-C5 aptamer, an anti-C5aR antibody and a C5aR antagonist.

10. The method of claim 9, wherein the C5aR antagonist is selected from the group consisting of: PMX-53, a PMX-53 analog, and combinations thereof.

11. The method of claim 1, wherein the acquired thrombophilia disorder is one of antiphospholipid syndrome and systemic lupus erythymatosus.

* * * * *